United States Patent [19]
Janjic et al.

[11] Patent Number: 5,668,264
[45] Date of Patent: *Sep. 16, 1997

[54] HIGH AFFINITY PDGF NUCLEIC ACID LIGANDS

[75] Inventors: Nebojsa Janjic; Larry Gold, both of Boulder, Colo.

[73] Assignee: NeXstar Pharmaceuticals, Inc., Boulder, Colo.

[*] Notice: The term of this patent shall not extend beyond the expiration date of Pat. No. 5,459,015.

[21] Appl. No.: 479,783

[22] Filed: Jun. 7, 1995

Related U.S. Application Data

[63] Continuation-in-part of Ser. No. 714,131, Jun. 10, 1991, Pat. No. 5,475,096, and a continuation-in-part of Ser. No. 931,473, Aug. 17, 1992, Pat. No. 5,270,163, and a continuation-in-part of Ser. No. 964,624, Oct. 21, 1992, Pat. No. 5,496,938, and a continuation-in-part of Ser. No. 117,991, Sep. 8, 1993, abandoned, said Ser. No. 714,131, is a continuation-in-part of Ser. No. 536,428, Jun. 11, 1990, abandoned.

[51] Int. Cl.$^6$ .................... C07H 21/02; C07H 21/04; C12Q 1/68; C12P 19/34
[52] U.S. Cl. .................... 536/23.1; 435/6; 435/91.2; 935/77; 935/78
[58] Field of Search .................... 435/6, 91.2; 536/23.1; 514/44

[56] References Cited

U.S. PATENT DOCUMENTS

| | | | |
|---|---|---|---|
| 4,683,195 | 7/1987 | Mullis et al. | 435/6 |
| 4,711,955 | 12/1987 | Ward et al. | 536/29 |
| 4,828,979 | 5/1989 | Klevan et al. | 435/6 |
| 4,935,363 | 6/1990 | Brown et al. | 435/172.3 |
| 5,070,010 | 12/1991 | Hsu et al. | 435/6 |
| 5,270,163 | 12/1993 | Gold et al. | 435/6 |
| 5,459,015 | 10/1995 | Janjic et al. | 435/6 |
| 5,475,096 | 12/1995 | Gold et al. | 536/22.1 |
| 5,476,766 | 12/1995 | Gold et al. | 435/6 |

FOREIGN PATENT DOCUMENTS

| | | |
|---|---|---|
| 2 183 661 | 6/1987 | United Kingdom . |
| WO/89/06694 | 7/1989 | WIPO . |
| WO/91/19813 | 6/1991 | WIPO . |
| WO/92/05285 | 4/1992 | WIPO . |
| WO/92/14843 | 9/1992 | WIPO . |

OTHER PUBLICATIONS

Vassbotn et al., *J. Cell Physiol.* 158(2):381–389 (Feb. 1994).
Johnsson, et al., *Proc. Natl. Acad. Sci., U.S.A.*, 82:1721 (1985).
Ferns, et al., *Science*, 253:1129 (1991).
Herren, et al., *Biochimica et Biophysica Acta*, 1173:294 (1993).
Duan, et al., *J. Biol. Chem.*, 266:413 (1991).
Teisman, et al., *J. Biol. Chem.*, 268:9621 (1993).
Williams, et al., *J. Biol. Chem.* 259:5287 (1984).
Betsholtz, et al., *Cell*, 39:447 (1984).
Vassbotn, *J. Biol. Chem.*, 267:15635 (1992).
Engstrom, *J. Biol. Chem.*, 267:16581 (1992).
Buchdunger, et al., *Proc. Natl. Acad. Sci. U.S.A.*, 92:2558 (1995).
Kovalenko, et al. *Cancer Res.*, 54:6106 (1994).
Joyce, *Gene*, 82:83 (1989).
Joyce and Inoue, *Nucleic Acids Research*, 17:711 (1989).
Ellington, et al., *Abstract of Papers presented at the 1990 meeting on RNA Processing*, Cold Spring Harbor Laboratory, Cold Spring Harbor, N.Y., pp. 226 (1990).
Kinzler, et al. *Nucleic Acids Research*, 17:3645 (1989).
Kramer, et al. *J. Mol. Biol.*, 89:719 (1974).
Levisohn, et al. *Proc. Natl. Acad. Sci.*, USA 63:805 (1969).
Levisohn, et al. *Proc. Natl. Acad. Sci.*, USA 60:866 (1968).
Oliphant, et al. *Mol. Cell. Biol.*, 9:2944 (1989).
Oliphant, et al. *Nucleic Acids Research*, 16:7673 (1988).
Oliphant, et al. *Methods in Enzymology*, 155:568 (1987).
Oliphant, et al. *Gene*, 44:177 (1986).
Robertson, et al. *Nature*, 344:467 (1990).
Thiesen, et al. *Nucleic Acids Research*, 18:3203 (1990).
Orgel, *Proc. R. Soc. Lond.*, B205:435 (1979).
Bass, et al., *Nature*, 308:820 (1984).
Carey, et al., *Biochemistry*, 22:2601 (1983).
Joyce, *RNA: Catalysis, Splicing, Evolution*, Belfort and Shub (eds.), Elsevier, Amsterdam pp. 83–87 (1989).
Kacian, et al., *Proc. Natl. Acad. Sci. USA*, 69:3038 (1972).
Mills, et al., *Science*, 180:916 (1973).
Mills, et al., *Proc. Natl. Acad. Sci. USA*, 58:217 (1967).
Rich, et al., *Ann. Rev. Biochem*, 53:791 (1984).
Robertson, et al., *Nature*, 344:467 (1990).
Romaniuk, et al., *Biochemistry*, 26:1563 (1987).
Saffhill, et al., *J. Mol. Biol.*, 51:531 (1970).
Schimmel, et al., *Cell*, 58:9 (1989).
Tuerk, et al., *Proc. Natl. Acad. Sci. USA*, 85:1364 (1988).
Uhlenbeck, et al., *J. Biomol. Structure and Dynamics*, 1:539 (1983).
Witherell, et al., *Biochemistry*, 28:71 (1989).
Yarus, *Science*, 240:1751 (1988).
Matthew, et al., *Analytical Biochemistry*, 169:1 (1988).
Andrake, et al., *Proc. Natl. Acad. Sci. USA*, 85:7924 (1988).
Cohen, et al., *Proc. Natl. Acad. Sci. USA*, 63:458 (1969).
Maniatis, et al., *Molec. Cloning: A Laboratory Manual*, Cold Spring Harbor, NY, p. 118 (1982).
Muesing, et al., *Nature*, 313:450 (1985).
Maniatis, et al., *Science*, 236:1237 (1987).
Watson, et al., *Molec. Biol. of the Gene*, Benjamin/Cummings Publishing Co., pp. 267, 295, 323, 361, 394, 396, 397, 405 (1987).
Ma, et al., *Cell*, 51:113 (1987).
Min, et al., *Nucl. Acids Res.*, 16:5075 (1988).
Ou, et al., *Science*, 239:295 (Jan. 15, 1988).
Lestienne, et al., *Biochimie*, 65:49 (1983).
Ellington, et al., *Nature*, 346:818 (1990).
Bock, et al., *Nature*, 355:564 (Feb. 6, 1992).
Stein, et al., *Science*, 261:1004 (Aug. 20, 1993).
Miele, et al., *J. Mol. Biol.*, 171:281–295.
Tuerk, et al., *Science*, 249:505 (1990).

Primary Examiner—Stephanie W. Zitomer
Attorney, Agent, or Firm—Swanson & Bratschun LLC

[57] ABSTRACT

Methods are described for the identification and preparation of high-affinity nucleic acid ligands to PDGF. Included in the invention are specific ssDNA and RNA ligands to PDGF identified by the SELEX method.

7 Claims, 1 Drawing Sheet

SEQUENCE LISTING ( 1 ) GENERAL INFORMATION:

( i i i ) NUMBER OF SEQUENCES: 90

( 2 ) INFORMATION FOR SEQ ID NO: 1:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 1:

```
ATCCGCCTGA TTAGCGATAC TNNNNNNNNN NNNNNNNNNN NNNNNNNNNN      50

NNNNNNNNNN NACTTGAGCA AAATCACCTG CAGGGG                      86
```

( 2 ) INFORMATION FOR SEQ ID NO: 2:

( i ) SEQUENCE CHARACTERISTICS:
        ( A ) LENGTH: 28 base pairs
        ( B ) TYPE: nucleic acid
        ( C ) STRANDEDNESS: single ( D ) TOPOLOGY: linear ( i i ) MOLECULE TYPE: DNA ( i x ) FEATURE:
                ( D ) OTHER INFORMATION: N at positions 1-3 is biotin ( x i ) SEQUENCE DESCRIPTION: SEQ ID NO: 2:

NNNCCCTGC AGGTGATTTT GCTCAAGT                                           2 8

( 2 ) INFORMATION FOR SEQ ID NO: 3:

( i ) SEQUENCE CHARACTERISTICS:
                ( A ) LENGTH: 49 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO: 3:

CCGAAGCTTA ATACGACTCA CTATAGGGAT CCGCCTGATT AGCGATACT                   4 9

( 2 ) INFORMATION FOR SEQ ID NO: 4:

( i ) SEQUENCE CHARACTERISTICS:
                ( A ) LENGTH: 84 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO: 4:

ATCCGCCTGA TTAGCGATAC TAGGCTTGAC AAAGGGCACC ATGGCTTAGT                   5 0

GGTCCTAGTA CTTGAGCAAA ATCACCTGCA GGGG                                    8 4

( 2 ) INFORMATION FOR SEQ ID NO: 5:

( i ) SEQUENCE CHARACTERISTICS:
                ( A ) LENGTH: 85 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO: 5:

ATCCGCCTGA TTAGCGATAC TCAGGGCACT GCAAGCAATT GTGGTCCCAA                   5 0

TGGGCTGAGT ACTTGAGCAA AATCACCTGC AGGGG                                   8 5

( 2 ) INFORMATION FOR SEQ ID NO: 6:

( i ) SEQUENCE CHARACTERISTICS:
                ( A ) LENGTH: 86 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO: 6:

ATCCGCCTGA TTAGCGATAC TCCAGGCAGT CATGGTCATT GTTTACAGTC                   5 0

GTGGAGTAGG TACTTGAGCA AAATCACCTG CAGGGG                                  8 6

( 2 ) INFORMATION FOR SEQ ID NO: 7:

( i ) SEQUENCE CHARACTERISTICS:
    ( A ) LENGTH: 85 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 7:

```
ATCCGCCTGA  TTAGCGATAC  TAGGTGATCC  CTGCAAAGGC  AGGATAACGT    50
CCTGAGCATC  ACTTGAGCAA  AATCACCTGC  AGGGG                     85
```

( 2 ) INFORMATION FOR SEQ ID NO: 8:

( i ) SEQUENCE CHARACTERISTICS:
    ( A ) LENGTH: 83 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 8:

```
ATCCGCCTGA  TTAGCGATAC  TATGTGATCC  CTGCAGAGGG  AGGANACGTC    50
TGAGCATCAC  TTGAGCAAAA  TCACCTGCAG  GGG                       83
```

( 2 ) INFORMATION FOR SEQ ID NO: 9:

( i ) SEQUENCE CHARACTERISTICS:
    ( A ) LENGTH: 86 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 9:

```
ATCCGCCTGA  TTAGCGATAC  TCACGTGATC  CCATAAGGGC  TGCGCAAAAT    50
AGCAGAGCAT  CACTTGAGCA  AAATCACCTG  CAGGGG                    86
```

( 2 ) INFORMATION FOR SEQ ID NO: 10:

( i ) SEQUENCE CHARACTERISTICS:
    ( A ) LENGTH: 86 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 10:

```
ATCCGCCTGA  TTAGCGATAC  TGGTGGACTA  GAGGGCAGCA  AACGATCCTT    50
GGTTAGCGTC  CACTTGAGCA  AAATCACCTG  CAGGGG                    86
```

( 2 ) INFORMATION FOR SEQ ID NO: 11:

( i ) SEQUENCE CHARACTERISTICS:
    ( A ) LENGTH: 85 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 11:

```
ATCCGCCTGA  TTAGCGATAC  TGGTGCGACG  AGGCTTACAC  AAACGTACAC    50
```

GTTCCCCGC ACTTGAGCAA AATCACCTGC AGGGG    85

( 2 ) INFORMATION FOR SEQ ID NO: 12:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 12:

ATCCGCCTGA TTAGCGATAC TTGTCGGAGC AGGGGCGTAC GAAAACTTTA    50

CAGTTCCCCC GACTTGAGCA AAATCACCTG CAGGGG    86

( 2 ) INFORMATION FOR SEQ ID NO: 13:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

ATCCGCCTGA TTAGCGATAC TAGTGGAACA GGGCACGGAG AGTCAAACTT    50

TGGTTTCCCC CACTTGAGCA AAATCACCTG CAGGGG    86

( 2 ) INFORMATION FOR SEQ ID NO: 14:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 14:

ATCCGCCTGA TTAGCGATAC TGTGGGTAGG GATCGGTGGA TGCCTCGTCA    50

CTTCTAGTCC CACTTGAGCA AAATCACCTG CAGGGG    86

( 2 ) INFORMATION FOR SEQ ID NO: 15:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 15:

ATCCGCCTGA TTAGCGATAC TGGGCGCCCT AAACAAAGGG TGGTCACTTC    50

TAGTCCCAGG AACTTGAGCA AAATCACCTG CAGGGG    86

( 2 ) INFORMATION FOR SEQ ID NO: 16:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 16:

```
ATCCGCCTGA TTAGCGATAC TTCCGGGCTC GGGATTCGTG GTCACTTTCA        50
GTCCCGGATA TAACTTGAGC AAAATCACCT GCAGGGG                      87
```

( 2 ) INFORMATION FOR SEQ ID NO: 17:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 17:

```
ATCCGCCTGA TTAGCGATAC TATGGGAGGG CGCGTTCTTC GTGGTTACTT        50
TTAGTCCCGA CTTGAGCAAA ATCACCTGCA GGGG                         84
```

( 2 ) INFORMATION FOR SEQ ID NO: 18:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 18:

```
ATCCGCCTGA TTAGCGATAC TACGGGAGGG CACGTTCTTC GTGGTTACTT        50
TTAGTCCCGA CTTGAGCAAA ATCACCTGCA GGGG                         84
```

( 2 ) INFORMATION FOR SEQ ID NO: 19:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 19:

```
ATCCGCCTGA TTAGCGATAC TGCTCGTAGG GGGCGATTCT TTCGCCGTTA        50
CTTCCAGTCC TACTTGAGCA AAATCACCTG CAGGGG                       86
```

( 2 ) INFORMATION FOR SEQ ID NO: 20:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 20:

```
ATCCGCCTGA TTAGCGATAC TGAGGCATGT TAACATGAGC ATCGTCTCAC        50
GATCCTCAGC CACTTGAGCA AAATCACCTG CAGGGG                       86
```

( 2 ) INFORMATION FOR SEQ ID NO: 21:

( i ) SEQUENCE CHARACTERISTICS:
        ( A ) LENGTH: 86 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 21:

```
ATCCGCCTGA TTAGCGATAC TCCACAGGCT ACGGCACGTA GAGCATCACC      50

ATGATCCTGT GACTTGAGCA AAATCACCTG CAGGGG                     86
```

(2) INFORMATION FOR SEQ ID NO: 22:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

```
ATCCGCCTGA TTAGCGATAC TGCGGGCATG GCACATGAGC ATCTCTGATC      50

CCGCAATCCT CACTTGAGCA AAATCACCTG CAGGGG                     86
```

(2) INFORMATION FOR SEQ ID NO: 23:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

```
ATCCGCCTGA TTAGCGATAC TACCGGGCTA CTTCGTAGAG CATCTCTGAT      50

CCCGGTGCTC GACTTGAGCA AAATCACCTG CAGGGG                     86
```

(2) INFORMATION FOR SEQ ID NO: 24:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

```
ATCCGCCTGA TTAGCGATAC TAAAGGGCGA ACGTAGGTCG AGGCATCCAT      50

TGGATCCCTT CACTTGAGCA AAATCACCTG CAGGGG                     86
```

(2) INFORMATION FOR SEQ ID NO: 25:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

```
ATCCGCCTGA TTAGCGATAC TACGGGCTCT GTCACTGTGG CACTAGCAAT      50

AGTCCCGTCG CACTTGAGCA AAATCACCTG CAGGGG                     86
```

( 2 ) INFORMATION FOR SEQ ID NO: 26:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 26:

```
ATCCGCCTGA   TTAGCGATAC   TGGGCAGACC   TTCTGGACGA   GCATCACCTA         50

TGTGATCCCG   ACTTGAGCAA   AATCACCTGC   AGGGG                            85
```

( 2 ) INFORMATION FOR SEQ ID NO: 27:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 27:

```
ATCCGCCTGA   TTAGCGATAC   TAGAGGGGAA   GTAGGCTGCC   TGACTCGAGA         50

GAGTCCTCCC   GACTTGAGCA   AAATCACCTG   CAGGGG                          86
```

( 2 ) INFORMATION FOR SEQ ID NO: 28:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 28:

```
ATCCGCCTGA   TTAGCGATAC   TAGGGGTGCG   AAACACATAA   TCCTCGCGGA         50

TTCCCATCGC   TACTTGAGCA   AAATCACCTG   CAGGGG                          86
```

( 2 ) INFORMATION FOR SEQ ID NO: 29:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 29:

```
ATCCGCCTGA   TTAGCGATAC   TGGGGGGGCA   ATGGCGGTAC   CTCTGGTCCC         50

CTAAATACAC   TTGAGCAAAA   TCACCTGCAG   GGG                             83
```

( 2 ) INFORMATION FOR SEQ ID NO: 30:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 30:

```
         ATCCGCCTGA TTAGCGATAC TGCGGCTCAA AGTCCTGCTA CCCGCAGCAC      50

ATCTGTGGTC ACTTGAGCAA AATCACCTGC AGGGG                      85
```

( 2 ) INFORMATION FOR SEQ ID NO: 31:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 31:

```
         ATCCGCCTGA TTAGCGATAC TTTGGGCGTG AATGTCCACG GGTACCTCCG      50

GTCCCAAAGA GACTTGAGCA AAATCACCTG CAGGGG                     86
```

( 2 ) INFORMATION FOR SEQ ID NO: 32:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 32:

```
         ATCCGCCTGA TTAGCGATAC TTCCGCGCAA GTCCCTGGTA AAGGGCAGCC      50

CTAACTGGTC ACTTGAGCAA AATCACCTGC AGGGG                      85
```

( 2 ) INFORMATION FOR SEQ ID NO: 33:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 33:

```
         ATCCGCCTGA TTAGCGATAC TCAAGTTCCC CACAAGACTG GGGCTGTTCA      50

AACCGCTAGT AACTTGAGCA AAATCACCTG CAGGGG                     86
```

( 2 ) INFORMATION FOR SEQ ID NO: 34:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 34:

```
         ATCCGCCTGA TTAGCGATAC TCAAGTAGGG CGCGACACAC GTCCGGGCAC      50

CTAAGGTCCC AACTTGAGCA AAATCACCTG CAGGGG                     86
```

( 2 ) INFORMATION FOR SEQ ID NO: 35:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 35:

```
ATCCGCCTGA TTAGCGATAC TAAAGTCGTG CAGGGTCCCC TGGAAGCATC        50

TCCGATCCCA GACTTGAGCA AAATCACCTG CAGGGG                       86
```

( 2 ) INFORMATION FOR SEQ ID NO: 36:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 36:

```
GGGAGACAAG AAUAACGCUC AANNNNNNNN NNNNNNNNNN NNNNNNNNNN        50

NNNNNNNNNN NNNNNNNNNN NNUUCGACAG GAGGCUCACA ACAGGC            96
```

( 2 ) INFORMATION FOR SEQ ID NO: 37:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 37:

```
TAATACGACT CACTATAGGG AGACAAGAAT AACGCTCAA                    39
```

( 2 ) INFORMATION FOR SEQ ID NO: 38:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 38:

```
GCCTGTTGTG AGCCTCCTGT CGAA                                    24
```

( 2 ) INFORMATION FOR SEQ ID NO: 39:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
        modified ( x i ) SEQUENCE DESCRIPTION: SEQ ID NO: 39:

```
GGGAGACAAG AAUAACGCUC AACGGUGGCA UUUCUUCACU UCCUUCUCGC        50

UUUCUCGCGU UGGGCNCGAU UCGACAGGAG GCUCACAACA GGC               93
```

( 2 ) INFORMATION FOR SEQ ID NO: 40:

( i ) SEQUENCE CHARACTERISTICS:
   ( A ) LENGTH: 91 base pairs
   ( B ) TYPE: nucleic acid
   ( C ) STRANDEDNESS: single
   ( D ) TOPOLOGY: linear ( i i ) MOLECULE TYPE: RNA ( i x ) FEATURE:
   ( D ) OTHER INFORMATION: All pyrimidines are 2'-F
      modified ( x i ) SEQUENCE DESCRIPTION: SEQ ID NO: 40:

```
GGGAGACAAG  AAUAACGCUC  AACCAACCUU  CUGUCGGCGU  UGCUUUUUGG        50
ACGGCACUCA  GGCUCCAUUC  GACAGGAGGC  UCACAACAGG  C                 91
```

( 2 ) INFORMATION FOR SEQ ID NO:41 :

( i ) SEQUENCE CHARACTERISTICS:
   ( A ) LENGTH: 95 base pairs
   ( B ) TYPE: nucleic acid
   ( C ) STRANDEDNESS: single
   ( D ) TOPOLOGY: linear ( i i ) MOLECULE TYPE: RNA ( i x ) FEATURE:
   ( D ) OTHER INFORMATION: All pyrimidines are 2'-F
      modified ( x i ) SEQUENCE DESCRIPTION: SEQ ID NO: 41:

```
GGGAGACAAG  AAUAACGCUC  AAUCGAUCGG  UUGUGUGCCG  GACAGCCUUA        50
ACCAGGGCUG  GGACCGAGGC  CUUCGACAGG  AGGCUCACAA  CAGGC             95
```

( 2 ) INFORMATION FOR SEQ ID NO: 42:

( i ) SEQUENCE CHARACTERISTICS:
   ( A ) LENGTH: 92 base pairs
   ( B ) TYPE: nucleic acid
   ( C ) STRANDEDNESS: single
   ( D ) TOPOLOGY: linear ( i i ) MOLECULE TYPE: RNA ( i x ) FEATURE:
   ( D ) OTHER INFORMATION: All pyrimidines are 2'-F
      modified ( x i ) SEQUENCE DESCRIPTION: SEQ ID NO: 42:

```
GGGAGACAAG  AAUAACGCUC  AACUGAGUAG  GGGAGGAAGU  UGAAUCAGUU        50
GUGGCGCCUC  UCAUUCGCUU  CGACAGGAGG  CUCACAACAG  GC                92
```

( 2 ) INFORMATION FOR SEQ ID NO: 43:

( i ) SEQUENCE CHARACTERISTICS:
   ( A ) LENGTH: 95 base pairs
   ( B ) TYPE: nucleic acid
   ( C ) STRANDEDNESS: single
   ( D ) TOPOLOGY: linear ( i i ) MOLECULE TYPE: RNA ( i x ) FEATURE:
   ( D ) OTHER INFORMATION: All pyrimidines are 2'-F
      modified ( x i ) SEQUENCE DESCRIPTION: SEQ ID NO: 43:

```
GGGAGACAAG  AAUAACGCUC  AACAGCACUU  UCGCUUUUCA  UCAUUUUUUC        50
UUUCCACUGU  UGGGCGCGGA  AUUCGACAGG  AGGCUCACAA  CAGGC             95
```

( 2 ) INFORMATION FOR SEQ ID NO: 44:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 44:

```
GGGAGACAAG  AAUAACGCUC  AAUCAGUGCU  GGCGUCAUGU  CUCGAUGGGG   50
AUUUUCUUC   AGCACUUUGC  CAUUCGACAG  GAGGCUCACA  ACAGGC       96
```

( 2 ) INFORMATION FOR SEQ ID NO: 45:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 45:

```
GGGAGACAAG  AAUAACGCUC  AAUCUACUUU  CCAUUUCUCU  UUUCUUCUCA   50
CGAGCGGGUU  UCCAGUGAAC  CAUUCGACAG  GAGGCUCACA  ACAGGC       96
```

( 2 ) INFORMATION FOR SEQ ID NO: 46:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 46:

```
GGGAGACAAG  AAUAACGCUC  AACGAUAGUG  ACUACGAUGA  CGAAGGCCGC   50
GGGUUGGAUG  CCCGCAUUGA  UUCGACAGGA  GGCUCACAAC  AGGC         94
```

( 2 ) INFORMATION FOR SEQ ID NO: 47:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 47:

```
        GGGAGACAAG  AAUAACGCUC  AAGUCGAUAC  UGGCGACUUG  CUCCAUUGGC      50

CGAUUAACGA  UUCGGUCAGU  UCGACAGGAG  GCUCACAACA  GGC             93
```

( 2 ) INFORMATION FOR SEQ ID NO: 48:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 48:

```
        GGGAGACAAG  AAUAACGCUC  AAGUGCAAAC  UUAACCCGGG  AACCGCGCGU      50

UUCGAUCGAC  UUUCCUUUCC  AUUCGACAGG  AGGCUCACAA  CAGGC           95
```

( 2 ) INFORMATION FOR SEQ ID NO: 49:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 49:

```
        GGGAGACAAG  AAUAACGCUC  AAAUUCCGCG  UUCCGAUUAA  UCCUGUGCUC      50

GGAAAUCGGU  AGCCAUAGUG  CAUUCGACAG  GAGGCUCACA  ACAGGC          96
```

( 2 ) INFORMATION FOR SEQ ID NO: 50:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 50:

```
        GGGAGACAAG  AAUAACGCUC  AACGAACGAG  GAGGGAGUGG  CAAGGGAUGG      50

UUGGAUAGGC  UCUACGCUCA  UUCGACAGGA  GGCUCACAAC  AGGC            94
```

( 2 ) INFORMATION FOR SEQ ID NO: 51:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:

(D) OTHER INFORMATION: All pyrimidines are 2'-F
modified (xi) SEQUENCE DESCRIPTION: SEQ ID NO: 51:

GGGAGACAAG AAUAACGCUC AAGCGAAACU GGCGACUUGC UCCAUUGGCC    50

GAUAUAACGA UUCGGUUCAU UUCGACAGGA GGCUCACAAC AGGC    94

(2) INFORMATION FOR SEQ ID NO: 52:

(i) SEQUENCE CHARACTERISTICS:
      (A) LENGTH: 95 base pairs
      (B) TYPE: nucleic acid
      (C) STRANDEDNESS: single
      (D) TOPOLOGY: linear (ii) MOLECULE TYPE: RNA (ix) FEATURE:
      (D) OTHER INFORMATION: All pyrimidines are 2'-F
          modified (xi) SEQUENCE DESCRIPTION: SEQ ID NO: 52:

GGGAGACAAG AAUAACGCUC AACGAACGAG GAGGGAGUCG CAAGGGAUGG    50

UUGGAUAGGC UCUACGCUCA AUUCGACAGG AGGCUCACAA CAGGC    95

(2) INFORMATION FOR SEQ ID NO: 53:

(i) SEQUENCE CHARACTERISTICS:
      (A) LENGTH: 94 base pairs
      (B) TYPE: nucleic acid
      (C) STRANDEDNESS: single
      (D) TOPOLOGY: linear (ii) MOLECULE TYPE: RNA (ix) FEATURE:
      (D) OTHER INFORMATION: All pyrimidines are 2'-F
          modified (xi) SEQUENCE DESCRIPTION: SEQ ID NO: 53:

GGGAGACAAG AAUAACGCUC AACGAGAAGU GACUACGAUG ACGAAGGCCG    50

CGGGUUGAAU CCCUCAUUGA UUCGACAGGA GGCUCACAAC AGGC    94

(2) INFORMATION FOR SEQ ID NO: 54:

(i) SEQUENCE CHARACTERISTICS:
      (A) LENGTH: 95 base pairs
      (B) TYPE: nucleic acid
      (C) STRANDEDNESS: single
      (D) TOPOLOGY: linear (ii) MOLECULE TYPE: RNA (ix) FEATURE:
      (D) OTHER INFORMATION: All pyrimidines are 2'-F
          modified (xi) SEQUENCE DESCRIPTION: SEQ ID NO: 54:

GGGAGACAAG AAUAACGCUC AAAAGCAACG AGACCUGACG CCUGAUGUGA    50

CUGUGCUUGC ACCGAUUCU GUUCGACAGG AGGCUCACAA CAGGC    95

(2) INFORMATION FOR SEQ ID NO: 55:

(i) SEQUENCE CHARACTERISTICS:
      (A) LENGTH: 96 base pairs
      (B) TYPE: nucleic acid
      (C) STRANDEDNESS: single
      (D) TOPOLOGY: linear ( i i ) MOLECULE TYPE: RNA ( i x ) FEATURE:
      ( D ) OTHER INFORMATION: All pyrimidines are 2'-F
            modified ( x i ) SEQUENCE DESCRIPTION: SEQ ID NO: 55:

```
GGGAGACAAG  AAUAACGCUC  AAGUGAUUCU  CAUUCUCAAU  GCUUCUCAC      50

AACUUUUCC   ACUUCAGCGU  GAUUCGACAG  GAGGCUCACA  ACAGGC         96
```

( 2 ) INFORMATION FOR SEQ ID NO: 56:

( i ) SEQUENCE CHARACTERISTICS:
       ( A ) LENGTH: 94 base pairs
       ( B ) TYPE: nucleic acid
       ( C ) STRANDEDNESS: single
       ( D ) TOPOLOGY: linear ( i i ) MOLECULE TYPE: RNA ( i x ) FEATURE:
       ( D ) OTHER INFORMATION: All pyrimidines are 2'-F
             modified ( x i ) SEQUENCE DESCRIPTION: SEQ ID NO: 56:

```
GGGAGACAAG  AAUAACGCUC  AAAAGCAACG  AGACUCGACG  CCUGAUGUGA     50

CUGUGCUUGC  ACCCGAUUCU  UUCGACAGGA  GGCUCACAAC  AGGC           94
```

( 2 ) INFORMATION FOR SEQ ID NO: 57:

( i ) SEQUENCE CHARACTERISTICS:
       ( A ) LENGTH: 96 base pairs
       ( B ) TYPE: nucleic acid
       ( C ) STRANDEDNESS: single
       ( D ) TOPOLOGY: linear ( i i ) MOLECULE TYPE: RNA ( i x ) FEATURE:
       ( D ) OTHER INFORMATION: All pyrimidines are 2'-F
             modified ( x i ) SEQUENCE DESCRIPTION: SEQ ID NO: 57:

```
GGGAGACAAG  AAUAACGCUC  AAUCGAUCGG  UUGUGUGCCG  GACAGCUUUG     50

ACCAUGAGCU  GGGACCGAGG  CCUUCGACAG  GAGGCUCACA  ACAGGC         96
```

( 2 ) INFORMATION FOR SEQ ID NO: 58:

( i ) SEQUENCE CHARACTERISTICS:
       ( A ) LENGTH: 96 base pairs
       ( B ) TYPE: nucleic acid
       ( C ) STRANDEDNESS: single
       ( D ) TOPOLOGY: linear ( i i ) MOLECULE TYPE: RNA ( i x ) FEATURE:
       ( D ) OTHER INFORMATION: All pyrimidines are 2'-F
             modified ( x i ) SEQUENCE DESCRIPTION: SEQ ID NO: 58:

```
GGGAGACAAG  AAUAACGCUC  AANGACGNGU  GGACCUGACU  AAUCGACUGA     50

UCAAAGAUCC  CGCCCAGAUG  GGUUCGACAG  GAGGCUCACA  ACAGGC         96
```

( 2 ) INFORMATION FOR SEQ ID NO: 59:

( i ) SEQUENCE CHARACTERISTICS:

(A) LENGTH: 94 base pairs
(B) TYPE: nucleic acid
(C) STRANDEDNESS: single
(D) TOPOLOGY: linear (ii) MOLECULE TYPE: RNA (ix) FEATURE:
(D) OTHER INFORMATION: All pyrimidines are 2'-F modified (xi) SEQUENCE DESCRIPTION: SEQ ID NO: 59:

```
GGGAGACAAG AAUAACGCUC AACACUGCGA CUUGCAGAAG CCUUGUGUGG      50
CGGUACCCCC UUUGGCCUCG UUCGACAGGA GGCUCACAAC AGGC            94
```

(2) INFORMATION FOR SEQ ID NO: 60:

(i) SEQUENCE CHARACTERISTICS:
(A) LENGTH: 94 base pairs
(B) TYPE: nucleic acid
(C) STRANDEDNESS: single
(D) TOPOLOGY: linear (ii) MOLECULE TYPE: RNA (ix) FEATURE:
(D) OTHER INFORMATION: All pyrimidines are 2'-F modified (xi) SEQUENCE DESCRIPTION: SEQ ID NO: 60:

```
GGGAGACAAG AAUAACGCUC AAGGUGGCAU UUCUUCAUUU UCCUUCUCGC      50
UUUCUCCGCC GUUGGGCGCG UUCGACAGGA GGCUCACAAC AGGC            94
```

(2) INFORMATION FOR SEQ ID NO: 61:

(i) SEQUENCE CHARACTERISTICS:
(A) LENGTH: 96 base pairs
(B) TYPE: nucleic acid
(C) STRANDEDNESS: single
(D) TOPOLOGY: linear (ii) MOLECULE TYPE: RNA (ix) FEATURE:
(D) OTHER INFORMATION: All pyrimidines are 2'-F modified (xi) SEQUENCE DESCRIPTION: SEQ ID NO: 61:

```
GGGAGACAAG AAUAACGCUC AACCUGAGUA GGGGGGAAAG UUGAAUCAGU      50
UGUGGCGCUC UACUCAUUCG CCUUCGACAG GAGGCUCACA ACAGGC          96
```

(2) INFORMATION FOR SEQ ID NO: 62:

(i) SEQUENCE CHARACTERISTICS:
(A) LENGTH: 94 base pairs
(B) TYPE: nucleic acid
(C) STRANDEDNESS: single
(D) TOPOLOGY: linear (ii) MOLECULE TYPE: RNA (ix) FEATURE:
(D) OTHER INFORMATION: All pyrimidines are 2'-F modified (xi) SEQUENCE DESCRIPTION: SEQ ID NO: 62:

```
GGGAGACAAG AAUAACGCUC AAGUCGAAAC UGGCGACUUG CUCCAUUGGC      50
CGAUAUAACG AUUCGGUUCA UUCGACAGGA GGCUCACAAC AGGC            94
```

( 2 ) INFORMATION FOR SEQ ID NO: 63:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F modified ( x i ) SEQUENCE DESCRIPTION: SEQ ID NO: 63:

```
GGGAGACAAG AAUAACGCUC AAGCGAUACU GGCGACUUGC UCCAUUGGCC      50
GAUAUAACGA UUCGGCUCAG UUCGACAGGA GGCUCACAAC AGGC            94
```

( 2 ) INFORMATION FOR SEQ ID NO: 64:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F modified ( x i ) SEQUENCE DESCRIPTION: SEQ ID NO: 64:

```
GGGAGACAAG AAUAACGCUC AAACGUGGGG CACAGGACCG AGAGUCCCUC      50
CGGCAAUAGC CGCUACCCCA CCUUCGACAG GAGGCUCACA ACAGGC          96
```

( 2 ) INFORMATION FOR SEQ ID NO: 65:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F modified ( x i ) SEQUENCE DESCRIPTION: SEQ ID NO: 65:

```
GGGAGACAAG AAUAACGCUC AACACAGCCU NANAGGGGGG AAGUUGAAUC      50
AGUUGUGGCG CUCUACUCAU UCGCUUCGAC AGGAGGCUCA CAACAGGC        98
```

( 2 ) INFORMATION FOR SEQ ID NO: 66:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F modified ( x i ) SEQUENCE DESCRIPTION: SEQ ID NO: 66:

|        |            |            |            |            |     |
|--------|------------|------------|------------|------------|-----|
| GGGAGACAAG | AAUAACGCUC | AAANGGGNUA | UGGUGACUUG | CUCCAUUGGC | 50  |
| CGAUAUAACG | AUUCGGUCAG | UUCGACAGGA | GGCUCACAAC | AGGC       | 94  |

( 2 ) INFORMATION FOR SEQ ID NO: 67:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 67:

|        |            |            |            |            |     |
|--------|------------|------------|------------|------------|-----|
| GGGAGACAAG | AAUAACGCUC | AACCUGCGUA | GGGNGGGAAG | UUGAAUCAGU | 50  |
| UGUGGCGCUC | UACUCAUUCG | CCUUCGACAG | GAGGCUCACA | ACAGGC     | 96  |

( 2 ) INFORMATION FOR SEQ ID NO: 68:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 68:

|        |            |            |            |            |     |
|--------|------------|------------|------------|------------|-----|
| GGGAGACAAG | AAUAACGCUC | AACGAACGAG | GAGGGAGUGG | CAAGGGAUGG | 50  |
| UUGGAUAGGC | UCUACGCUCA | UUCGACAGGA | GGCUCACAAC | AGGC       | 94  |

( 2 ) INFORMATION FOR SEQ ID NO: 69:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F
            modified ( x i ) SEQUENCE DESCRIPTION: SEQ ID NO: 69:

|        |            |            |            |            |     |
|--------|------------|------------|------------|------------|-----|
| GGGAGACAAG | AAUAACGCUC | AAGUGCAAAC | UUAACCCGGG | AACCGCGCGU | 50  |
| UUCGAUUCGC | UUUCCNUAUU | CCAUUCGACA | GGAGGCUCAC | AACAGGC    | 97  |

( 2 ) INFORMATION FOR SEQ ID NO: 70:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-F -continued modified ( x i ) SEQUENCE DESCRIPTION: SEQ ID NO: 70:

GGGAGACAAG AAUAACGCUC AACGAACGAG GAGGGAGUGG CAAGGGACGG 50

UNNAUAGGCU CUACGCUCAU UCGACAGGAG GCUCACAACA GGC 93

( 2 ) INFORMATION FOR SEQ ID NO: 71:

( i ) SEQUENCE CHARACTERISTICS:
      ( A ) LENGTH: 93 base pairs
      ( B ) TYPE: nucleic acid
      ( C ) STRANDEDNESS: single
      ( D ) TOPOLOGY: linear ( i i ) MOLECULE TYPE: RNA ( i x ) FEATURE:
      ( D ) OTHER INFORMATION: All pyrimidines are 2'-F modified ( x i ) SEQUENCE DESCRIPTION: SEQ ID NO: 71:

GGGAGACAAG AAUAACGCUC AAUCGGUGUG GCUCAGAAAC UGACACGCGU 50

GAGCUUCGCA CACAUCUGCU UCGACAGGAG GCUCACAACA GGC 93

( 2 ) INFORMATION FOR SEQ ID NO: 72:

( i ) SEQUENCE CHARACTERISTICS:
      ( A ) LENGTH: 95 base pairs
      ( B ) TYPE: nucleic acid
      ( C ) STRANDEDNESS: single
      ( D ) TOPOLOGY: linear ( i i ) MOLECULE TYPE: RNA ( i x ) FEATURE:
      ( D ) OTHER INFORMATION: All pyrimidines are 2'-F modified ( x i ) SEQUENCE DESCRIPTION: SEQ ID NO: 72:

GGGAGACAAG AAUAACGCUC AAUAUCGCUU UCAUCAAUU CCACUUUUUC 50

ACUCUNUAAC UUGGGCGUGC AUUCGACAGG AGGCUCACAA CAGGC 95

( 2 ) INFORMATION FOR SEQ ID NO: 73:

( i ) SEQUENCE CHARACTERISTICS:
      ( A ) LENGTH: 96 base pairs
      ( B ) TYPE: nucleic acid
      ( C ) STRANDEDNESS: single
      ( D ) TOPOLOGY: linear ( i i ) MOLECULE TYPE: RNA ( i x ) FEATURE:
      ( D ) OTHER INFORMATION: All pyrimidines are 2'-F modified ( x i ) SEQUENCE DESCRIPTION: SEQ ID NO: 73:

GGGAGACAAG AAUAACGCUC AAGUGCAAAC UUAACCCGGG AACCGCGCGU 50

UUCGAUCCUG CAUCCUUUUU CCUUCGACAG GAGGCUCACA ACAGGC 96

( 2 ) INFORMATION FOR SEQ ID NO: 74:

( i ) SEQUENCE CHARACTERISTICS:
      ( A ) LENGTH: 93 base pairs
      ( B ) TYPE: nucleic acid
      ( C ) STRANDEDNESS: single
      ( D ) TOPOLOGY: linear ( i i ) MOLECULE TYPE: RNA ( i x ) FEATURE:
      ( D ) OTHER INFORMATION: All pyrimidines are 2'-F
          modified ( x i ) SEQUENCE DESCRIPTION: SEQ ID NO: 74:

```
GGGAGACAAG AAUAACGCUC AAUCGNUCGG UUGUGUGCCG GCAGCUUUGU      50
CCAGCGUUGG GCCGAGGCCU UCGACAGGAG GCUCACAACA GGC             93
```

( 2 ) INFORMATION FOR SEQ ID NO: 75:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
      ( D ) OTHER INFORMATION: All pyrimidines are 2'-F
          modified ( x i ) SEQUENCE DESCRIPTION: SEQ ID NO: 75:

```
GGGAGACAAG AAUAACGCUC AAAGUACCCA UCUCAUCUUU UCCUUUCCUU      50
UCUUCAAGGC ACAUUGAGGG UUUCGACAGG AGGCUCACAA CAGGC           95
```

( 2 ) INFORMATION FOR SEQ ID NO: 76:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
      ( D ) OTHER INFORMATION: All pyrimidines are 2'-F
          modified ( x i ) SEQUENCE DESCRIPTION: SEQ ID NO: 76:

```
GGGAGACAAG AAUAACGCUC AACCUGAGUA GGGGGGGAAG UUGAACCAGU      50
UGUGGCNGCC UACUCAUUCN CCAUUCGACA GGAGGCUCAC AACAGGC         97
```

( 2 ) INFORMATION FOR SEQ ID NO: 77:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
      ( D ) OTHER INFORMATION: All pyrimidines are 2'-F
          modified ( x i ) SEQUENCE DESCRIPTION: SEQ ID NO: 77:

```
GGGAGACAAG AAUAACGCUC AACCNNCCUN CUGUCGGCGC UUGUCUUUUU      50
GGACGGGCAA CCCAGGGCUC UUCGACAGGA GGCUCACAAC AGGC            94
```

( 2 ) INFORMATION FOR SEQ ID NO: 78:

( i ) SEQUENCE CHARACTERISTICS:
        ( A ) LENGTH: 96 base pairs ( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All pyrimidines are 2'-F
modified ( x i ) SEQUENCE DESCRIPTION: SEQ ID NO: 78:

```
GGGAGACAAG  AAUAACGCUC  AACCAACCUN  CUGUCGGCGC  UUGUCUUUUU         50

GGACGAGCAA  CUCAAGGCUC  GUUUCGACAG  GAGGCUCACA  ACAGGC             96
```

( 2 ) INFORMATION FOR SEQ ID NO: 79:

( i ) SEQUENCE CHARACTERISTICS:
( A ) LENGTH: 93 base pairs
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All pyrimidines are 2'-F
modified ( x i ) SEQUENCE DESCRIPTION: SEQ ID NO: 79:

```
GGGAGACAAG  AAUAACGCUC  AACCAGCGCA  GAUCCCGGGC  UGAAGUGACU         50

GCCGGCAACG  GCCGCUCCAU  UCGACAGGAG  GCUCACAACA  GGC                93
```

( 2 ) INFORMATION FOR SEQ ID NO: 80:

( i ) SEQUENCE CHARACTERISTICS:
( A ) LENGTH: 96 base pairs
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All pyrimidines are 2'-F
modified ( x i ) SEQUENCE DESCRIPTION: SEQ ID NO: 80:

```
GGGAGACAAG  AAUAACGCUC  AAUUCCCGUA  ACAACUUUUC  AUUUUCACUU         50

UUCAUCCAAC  CAGUGAGCAG  CAUUCGACAG  GAGGCUCACA  ACAGGC             96
```

( 2 ) INFORMATION FOR SEQ ID NO: 81:

( i ) SEQUENCE CHARACTERISTICS:
( A ) LENGTH: 96 base pairs
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All pyrimidines are 2'-F
modified ( x i ) SEQUENCE DESCRIPTION: SEQ ID NO: 81:

```
GGGAGACAAG  AAUAACGCUC  AAUAUCGCUU  UCAUCAAAUU  CCACUCCUUC         50

ACUUCUUUAA  CUUGGGCGUG  CAUUCGACAG  GAGGCUCACA  ACAGGC             96
```

( 2 ) INFORMATION FOR SEQ ID NO: 82:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: Nucleotide 44 is an inverted
            orientation T (3'-3'linked)

( x i ) SEQUENCE DESCRIPTION: SEQ ID NO: 82:

```
TACTAGGCTT GACAAAGGGC ACCATGGCTT AGTGGTCCTA GTAT                44
```

( 2 ) INFORMATION FOR SEQ ID NO: 83:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: Nucleotide 38 is an inverted
            orientation T (3'-3'linked)

( x i ) SEQUENCE DESCRIPTION: SEQ ID NO: 83:

```
TGGGAGGGCG CGTTCTTCGT GGTTACTTTT AGTCCCGT                       38
```

( 2 ) INFORMATION FOR SEQ ID NO: 84:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: Nucleotide 33 is an inverted
            orientation T (3'-3'linked)

( x i ) SEQUENCE DESCRIPTION: SEQ ID NO: 84:

```
GGGCGCGTTC TTCGTGGTTA CTTTTAGTCC CGT                            33
```

( 2 ) INFORMATION FOR SEQ ID NO: 85:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( D ) OTHER INFORMATION: Nucleotide 45 is an inverted
            orientation T (3'-3'linked)

( x i ) SEQUENCE DESCRIPTION: SEQ ID NO: 85:

```
TACTCAGGGC ACTGCAAGCA ATTGTGGTCC CAATGGGCTG AGTAT               45
```

( 2 ) INFORMATION FOR SEQ ID NO: 86:

( i ) SEQUENCE CHARACTERISTICS:
        ( A ) LENGTH: 41 base pairs (B) TYPE: nucleic acid
(C) STRANDEDNESS: single
(D) TOPOLOGY: linear (ii) MOLECULE TYPE: DNA (ix) FEATURE:
(D) OTHER INFORMATION: Nucleotide 41 is an inverted
orientation T (3'-3'linked)

(xi) SEQUENCE DESCRIPTION: SEQ ID NO: 86:

CCACAGGCTA CGGCACGTAG AGCATCACCA TGATCCTGTG T                41

(2) INFORMATION FOR SEQ ID NO: 87:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: DNA (ix) FEATURE:
(D) OTHER INFORMATION: Nucleotide 44 is an inverted
orientation T (3'-3'linked)

(xi) SEQUENCE DESCRIPTION: SEQ ID NO: 87:

AGTGGAACAG GGCACGGAGA GTCAAACTTT GGTTTCCCCC ACTT             44

(2) INFORMATION FOR SEQ ID NO: 88:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: DNA (ix) FEATURE:
(D) OTHER INFORMATION: Nucleotide 44 is an inverted
orientation T (3'-3'linked)

(xi) SEQUENCE DESCRIPTION: SEQ ID NO: 88:

AAGTCGTGCA GGGTCCCCTG GAAGCATCTC CGATCCAGA CTTT              44

(2) INFORMATION FOR SEQ ID NO: 89:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (ix) FEATURE:
(D) OTHER INFORMATION: Nucleotide 35 is an inverted
orientation T (3'-3'linked)

(xi) SEQUENCE DESCRIPTION: SEQ ID NO: 89:

TAGAGGGGAA GTAGGCTGCC TGACTCGAGA GAGTT                        35

(2) INFORMATION FOR SEQ ID NO: 90:

(i) SEQUENCE CHARACTERISTICS:
(A) LENGTH: 39 base pairs
(B) TYPE: nucleic acid
(C) STRANDEDNESS: single
(D) TOPOLOGY: linear (i i) MOLECULE TYPE: DNA (i x) FEATURE:
(D) OTHER INFORMATION: Nucleotide 39 is an inverted orientation T (3'-3'linked)

(x i) SEQUENCE DESCRIPTION: SEQ ID NO: 90:

CAGTCCGTGG TAGGGCAGGT TGGGGTGACT TCGTGGAAT       39

HIGH AFFINITY PDGF NUCLEIC ACID LIGANDS

RELATED APPLICATIONS

This application is a Continuation-in-Part of U.S. patent application Ser. No. 07/714,131, filed Jun. 10, 1991, entitled Nucleic Acid Ligands, now issued as U.S. Pat. No. 5,475,096 U.S. patent application Ser. No. 07/931,473, filed Aug. 17, 1992, entitled Nucleic Acid Ligands, now issued as U.S. Pat. No. 5,270,163, U.S. patent application Ser. No. 07/964,624, filed Oct. 21, 1992, entitled Methods of Producing Nucleic Acid Ligands, now issued as U.S. Pat. No. 5,496,938 and U.S. patent application Ser. No. 08/117,991, filed Sep. 8, 1993, entitled High-Affinity Nucleic Acid Ligands Containing Modified Nucleotides, now abandoned. U.S. patent application Ser. No. 07/714,131, U.S. Pat. No. 5,475,096 is a Continuation-in-Part of U.S. patent application Ser. No. 07/536,428, filed Jun. 11, 1990, entitled Systematic Evolution of Ligands by EXponential Enrichment, now abandoned.

FIELD OF THE INVENTION

Described herein are methods for identifying and preparing high-affinity nucleic acid ligands to PDGF. The method utilized herein for identifying such nucleic acid ligands is called SELEX, an acronym for Systematic Evolution of Ligands by EXponential enrichment. This invention includes high affinity nucleic acid ligands of PDGF. Further disclosed are ssDNA and RNA ligands to PDGF. The oligonucleotides of the present invention are useful as pharmaceuticals or diagnostic agents.

BACKGROUND OF THE INVENTION

Platelet-derived growth factor (PDGF) was originally isolated from platelet lysates and identified as the major growth-promoting activity present in serum but not in plasma. Two homologous PDGF isoforms have been identified, PDGF A and B, which are encoded by separate genes (on chromosomes 7 and 22). The most abundant species from platelets is the AB heterodimer, although all three possible dimers (AA, AB and BB) occur naturally. Following translation, PDGF dimers are processed into ≈30 kDa secreted proteins. Two cell surface proteins that bind PDGF with high affinity have been identified, $\alpha$ and $\beta$ (Heldin et al., *Proc. Natl. Acad. Sci.*, 78: 3664 (1981); Williams et al., *Proc. Natl. Acad. Sci.*, 79: 5867 (1981)). Both species contain five immunoglobulin-like extracellular domains, a single transmembrane domain and an intracellular tyrosine kinase domain separated by a kinase insert domain. The functional high affinity receptor is a dimer and engagement of the extracellular domain of the receptor by PDGF results in cross-phosphorylation (one receptor tyrosine kinase phosphorylates the other in the dimer) of several tyrosine residues. Receptor phosphorylation leads to a cascade of events that results in the transduction of the mitogenic or chemotactic signal to the nucleus. For example, in the intracellular domain of the PDGF $\beta$ receptor, nine tyrosine residues have been identified that when phosphorylated interact with different src-homology 2 (SH2) domain-containing proteins including phospholipase C-$\gamma$, phosphatidylinositol 3'-kinase, GTPase-activating protein and several adaptor molecules like Shc, Grb2 and Nck (Heldin, *Cell*, 80: 213 (1995)). In the last several years, the specificities of the three PDGF isoforms for the three receptor dimers ($\alpha\alpha$, $\alpha\beta$, and $\beta\beta$) has been elucidated. The $\alpha$-receptor homodimer binds all three PDGF isoforms with high affinity, the $\beta$-receptor homodimer binds only PDGF BB with high affinity and PDGF AB with approximately 10-fold lower affinity, and the $\alpha\beta$-receptor heterodimer binds PDGF BB and PDGF AB with high affinity (Westermark & Heldin, *Acta Oncologica*, 32: 101 (1993)). The specificity pattern results from the ability of the A-chain to bind only to the $\alpha$-receptor and of the B-chain to bind to both $\alpha$ and $\beta$-receptor subunits with high affinity.

The earliest indication that PDGF expression is linked to malignant transformation came with the finding that the amino acid sequence of PDGF-B chain is virtually identical to that of $p28^{sis}$, the transforming protein of the simian sarcoma virus (SSV) (Waterfield et al., *Nature*, 304: 35 (1983); Johnsson et al., *EMBO J.*, 3: 921 (1984)). The transforming potential of the PDGF-B chain gene and, to a lesser extent, the PDGF-A gene was demonstrated soon thereafter (Clarke et al., *Nature*, 308: 464 (1984); Gazit et al., *Cell*, 39: 89 (1984); Beckmann et al., *Science*, 241: 1346; Bywater et al., *Mol. Cell. Biol.*, 8: 2753 (1988)). Many tumor cell lines have since been shown to produce and secrete PDGF, some of which also express PDGF receptors (Raines et al., *Peptide Growth Factors and Their Receptors*, Springer-Verlag, Part I, p 173 (1990)). Paracrine and, in some cell lines, autocrine growth stimulation by PDGF is therefore possible. For example, analysis of biopsies from human gliomas has revealed the existence of two autocrine loops: PDGF-B/$\beta$-receptor in tumor-associated endothelial cells and PDGF-A/$\alpha$-receptor in tumor cells (Hermansson et al., *Proc. Natl. Acad. Sci.*, 85: 7748 (1988); Hermansson et al., *Cancer Res.*, 52: 3213 (1992)). The progression to high grade glioma was accompanied by the increase in expression of PDGF-B and the $\beta$-receptor in tumor-associated endothelial cells and PDGF-A in glioma cells. Increased expression of PDGF and/or PDGF receptors has also been observed in other malignancies including fibrosarcoma (Smits et al., *Am. J. Pathol.*, 140: 639 (1992)) and thyroid carcinoma (Heldin et al., *Endocrinology*, 129: 2187 (1991)).

Although the contribution of PDGF in the progression of several proliferative disease states has been recognized (Heldin, *EMBO J.*, 11, 4251 (1992); Raines et al., supra), there is a relative paucity of effective inhibitors of PDGF. The identification of novel antagonists of PDGF is therefore highly desirable. Currently, antibodies are the most potent antagonists of PDGF that have been described. Neutralizing antibodies to PDGF have been shown to revert the SSV-transformed phenotype (Johnsson et al., *Proc. Natl. Acad. Sci. U.S.A.*, 82: 1721 (1985)) and to inhibit the development of neointimal lesions following arterial injury (Ferns et al., *Science*, 253: 1129 (1991)). Other inhibitors that have been described to date include suramin (an aromatic hexaanion, which also inhibits many other growth factors and is relatively toxic), and neomycin, which at high concentrations (5 mM) inhibits binding of PDGF BB to the $\alpha$- but not the $\beta$-receptor (Williams et al., *J. Biol. Chem.*, 259: 5287 (1984); Vassbotn et al., *J. Biol. Chem.*, 267: 15635 (1992)).

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment," now abandoned, U.S. patent application Ser. No. 07/714,131, filed Jun. 10, 1991, entitled "Nucleic Acid Ligands," now U.S. Pat. No. 5,475,096 U.S. patent application Ser. No. 07/931,473, filed Aug. 17, 1992, entitled "Nucleic Acid Ligands," now U.S. Pat. No. 5,270,163 (see also WO Publication No. 91/19813), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands" describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," now U.S. Pat. No. 5,567,588 describes a SELEX-based method which achieves highly efficient partitioning between oligonucleotides having high and low affinity for a target molecule. U.S. patent application Ser. No. 07/964,624, filed Oct. 21, 1992, entitled "Methods of Producing Nucleic Acid Ligands" now U.S. Pat. No. 5,496,938 describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" and U.S. patent application Ser. No. 08/234,997, filed Apr. 28, 1994, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

In the present invention, the identification of high-affinity nucleic acid ligands to PDGF is described. Specifically, single stranded DNA ligands and 2'-fluoropyrimidine RNA ligands to PDGF are described.

BRIEF SUMMARY OF THE INVENTION

The present invention includes methods of identifying and producing nucleic acid ligands to platelet-derived growth factor (PDGF) and homologous proteins and the nucleic acid ligands so identified and produced. For the purposes of this application, PDGF refers to PDGF AA, AB, and BB isoforms and homologous proteins. Specifically included in the definition are human PDGF AA, AB, and BB isoforms. Specifically included in the invention are the ssDNA ligand sequences shown in Table 2 (SEQ ID NOS:) 4–35. Further included in the invention are the RNA ligand sequences shown in Table 5 (SEQ ID NOS:) 39–81.

Further included in this invention is a method of identifying nucleic acid ligands and nucleic acid ligand sequences to PDGF comprising the steps of (a) preparing a candidate mixture of nucleic acids, (b) contacting the candidate mixture of nucleic acids with PDGF, (c) partitioning between members of said candidate mixture on the basis of affinity to PDGF, and (d) amplifying the selected molecules to yield a mixture of nucleic acids enriched for nucleic acid sequences with a relatively higher affinity for binding to PDGF.

More specifically, the present invention includes the ssDNA and RNA ligands to PDGF identified according to the above-described method, including those ligands shown in Tables 2 and 5 (SEQ ID NOS:) 4–35; 39–81. Also included are DNA and RNA ligands to PDGF that are substantially homologous to any of the given ligands and that have substantially the same ability to bind PDGF. Further included in this invention are nucleic acid ligands to PDGF that have substantially the same structural form as the ligands presented herein and that have substantially the same ability to bind PDGF.

The present invention also includes modified nucleotide sequences based on the ssDNA and RNA ligands identified herein and mixtures of the same.

DETAILED DESCRIPTION OF THE INVENTION

Figure 1:
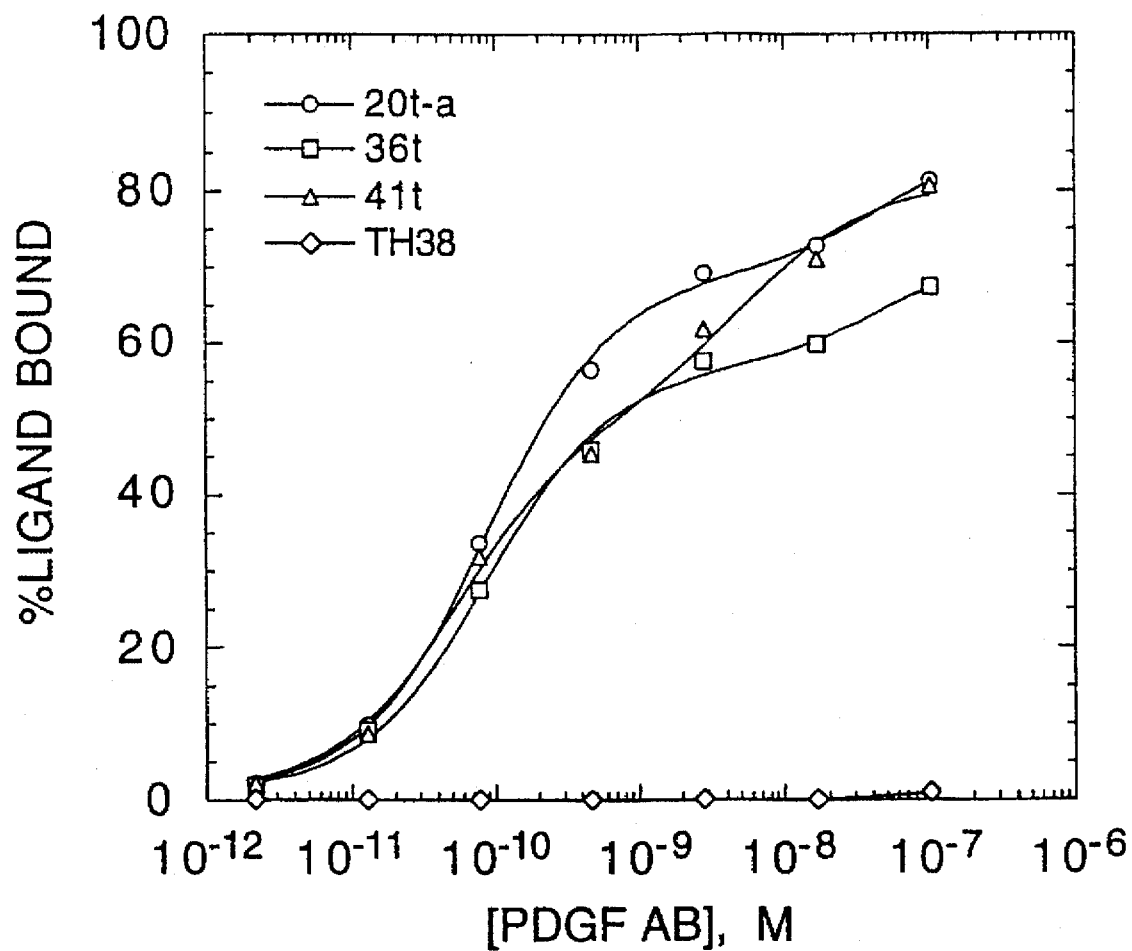
FIG. 1 shows binding of high-affinity ssDNA ligands 20t-a, 36t, and 41t to PDGF AB at varying concentrations of PDGF AB. Binding to PDGF AB of a ssDNA ligand (TH38) that binds to human thrombin with high affinity is shown for comparison.

This application describes high-affinity nucleic acid ligands to PDGF identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096 U.S. patent application Ser. No. 07/931,473, filed Aug. 17, 1992, entitled Nucleic Acid Ligands, now U.S. Pat. No. 5,270,163, (see also WO Publication No. 91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The nucleic acid ligands described herein can be complexed with a lipophilic compound (e.g., cholesterol) or attached to or encapsulated in a complex comprised of lipophilic components (e.g., a liposome). The complexed nucleic acid ligands can enhance the cellular uptake of the nucleic acid ligands by a cell for delivery of the nucleic acid ligands to an intracellular target. U.S. patent application Ser. No. 08/434,465, filed May 4, 1995, entitled "Nucleic Acid Ligand Complexes," which is incorporated in its entirety herein, describes a method for preparing a therapeutic or diagnostic complex comprised of a nucleic acid ligand and a lipophilic compound or a non-immunogenic, high molecular weight compound.

The methods described herein and the nucleic acid ligands identified by such methods are useful for both therapeutic and diagnostic purposes. Therapeutic uses include the treatment or prevention of diseases or medical conditions in human patients. Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to PDGF described herein may specifically be used for identification of the PDGF protein.

SELEX provides high affinity ligands of a target molecule. This represents a singular achievement that is unprecedented in the field of nucleic acids research. The present invention applies the SELEX procedure to the specific target of PDGF. In the Example section below, the experimental parameters used to isolate and identify the nucleic acid ligands to PDGF are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624) now U.S. Pat. No. 5,496,938, methods are described for obtaining improved nucleic acid ligands after SELEX has been performed. The '624 application, entitled Methods of Producing Nucleic Acid Ligands, is specifically incorporated herein by reference.

In the present invention, two SELEX experiments were performed in order to identify ssDNA and RNA with specific high affinity for PDGF from degenerate libraries containing 40 and 50 random positions (40N SEQ ID NO: 1 and 50N SEQ ID NO: 36), respectively (Tables 1 and 4). This invention includes the specific ssDNA and RNA ligands to PDGF shown in Tables 2 and 5 (SEQ ID NOS: 4–35; 39–81), identified by the methods described in Examples 1 and 3. The scope of the ligands covered by this invention extends to all nucleic acid ligands of PDGF, modified and unmodified, identified according to the SELEX procedure. More specifically, this invention includes nucleic acid sequences that are substantially homologous to the ligands shown in Tables 2 and 5 (SEQ ID NOS: 4–35; 39–81). By substantially homologous it is meant a degree of primary sequence homology in excess of 70%, most preferably in excess of 80%. A review of the sequence homologies of the ligands of PDGF shown in Tables 2 and 5 (SEQ ID NOS: 4–35; 39–81) shows that sequences with little or no primary homology may have substantially the same ability to bind PDGF. For these reasons, this invention also includes nucleic acid ligands that have substantially the same structure and ability to bind PDGF as the nucleic acid ligands shown in Tables 2 and 5 (SEQ ID NOS: 4–35; 39–81). Substantially the same ability to bind PDGF means that the affinity is within one or two orders of magnitude of the affinity of the ligands described herein. It is well within the skill of those of ordinary skill in the art to determine whether a given sequence—substantially homologous to those specifically described herein—has substantially the same ability to bind PDGF.

This invention also includes the ligands as described above, wherein certain chemical modifications are made in order to increase the in vivo stability of the ligand or to enhance or mediate the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 9, 1993, entitled High Affinity Nucleic Acid Ligands Containing Modified Nucleotides which is specifically incorporated herein by reference. Other modifications are known to one of ordinary skill in the art. Such modifications may be made post-SELEX (modification of previously identified unmodified ligands) or by incorporation into the SELEX process.

As described above, because of their ability to selectively bind PDGF, the nucleic acid ligands to PDGF described herein are useful as pharmaceuticals. This invention, therefore, also includes a method for treating PDGF-mediated diseases by administration of a nucleic acid ligand capable of binding to PDGF.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

The following Examples are provided to explain and illustrate the present invention and are not intended to be limiting of the invention. Example 1 describes the various materials and experimental procedures used in evolving ssDNA ligands to PDGF described in Example 2. Example 2 describes the ssDNA ligands to PDGF, and the minimal sequence determination for selected ligands. Example 3 describes the experimental procedures used in evolving RNA ligands to PDGF and shows the ligand sequences.

EXAMPLE 1

EXPERIMENTAL PROCEDURES

Materials

Recombinant human PDGF AB was purchased from R&D Systems (Minneapolis, Minn., catalog number 222-AB). All other reagents, chemicals and plasmids were from commercial sources. 2'-fluoro-2'-deoxypyrimidine nucleoside triphosphates used in the 2'fluoro-2'-deoxypyrimidine SELEX experiment were prepared as described in Pieken et al. (1991) Science 253: 314–317.

SINGLE STRANDED DNA (SSDNA) SELEX

Essential features of the SELEX procedure have been described in detail in the SELEX Patent Applications (see also Tuerk and Gold, *Science*, 249: 505 (1990); Jellinek et al., *Biochemistry*, 33: 10450 (1994); Jellinek et al., *Proc. Natl. Acad. Sci.*, 90: 11227 (1993), which are incorporated by reference herein). In this experiment, the SELEX protocol was performed in a similar manner with single stranded DNA (ssDNA). For all affinity selections, recombinant human PDGF AB was used. Briefly, SELEX was initiated by incubating approximately 500 pmol of ssDNA containing a contiguous randomized region with PDGF AB in phosphate buffered saline (PBS=10.1 mM $Na_2HPO_4$, 1.8 mM $KH_2PO_4$, 137 mM NaCl and 2.7 mM KCl, pH 7.4) containing 0.01% human serum albumin and 1 mM $MgCl_2$. The mixture of PDGF AB and the random DNA pool was incubated at 4° C. overnight, followed by a brief (15 min) incubation at 37° C. and the DNA bound to the protein was then resolved from the free DNA by electrophoresis on 8% non-denaturing polyacrylamide gel (1:30 bis-acrylamide:acrylamide). Subsequent affinity selections were done using the nitrocellulose filter partitioning method as described (Jellinek et al., 1994). Prior to the incubation with PDGF, the ssDNA was heated in PBS at 90° C. for 2 minutes and cooled on ice. All affinity selections were done by incubating PDGF with ssDNA for at least 15 minutes at 37° C. in PBS containing 0.01% human serum albumin and 1 mM $MgCl_2$. The ssDNA template (40N2) SEQ ID NO: 1 containing 40 random nucleotides flanked by invariant primer annealing sites was amplified by polymerase chain reaction (PCR) utilizing oligos 3N2 SEQ ID NO: 2 and [γ-$^{32}$P]ATP end labeled 5N2 SEQ ID NO: 3 (Table 1). Oligo 3N2 was synthesized with three biotin moieties covalently attached to its 5' terminus in order to separate 40N2 from its complement after thermal cycling. This was achieved by incubating the PCR reaction in the presence of a 10 fold molar excess of streptavidin (Pierce, Rockford, Ill.) over the biotinylated 3N2 oligo. The labeled non-biotinylated ssDNA 40N2 was then separated from the streptavidin labeled complement strand based on the mobility difference between the biotinylated and the non-biotinylated strands on 12% polyacrylamide gel containing 7M urea. The faster migrating non-biotinylated ssDNA strand was cut out of the gel, eluted by the crush and soak method, alcohol precipitated, pelleted by centrifugation, the pellet dried under vacuum and resuspended in PBS buffer. The amount of ssDNA was determined from the absorbance at 260 nm using the extinction coefficient of 33 µg/ml/absorbance unit. After 12 rounds of selection, an affinity of greater than two orders of magnitude was observed (data not shown). Individual members of the affinity-enriched pool were cloned and sequenced as described in Jellinek et al., 1993, 1994: supra; Schneider et al., *J. Mol. Biol.*, 188: 415 (1992).

EXAMPLE 2 ssDNA LIGANDS OF PDGF

All isolates from the affinity-enriched pool with unique sequences are shown in Table 2 SEQ ID NOS: 4–35. The ligands were grouped into three families according to primary structure similarity in the evolved sequence region (Jellinek et al., 1994: supra). Primary structure conservation is limited even among sequences grouped in the same family. Family 2 ligands were split into three subfamilies. Ligands whose sequences did not contain significant similarity with other ligands were placed in the "Other Sequences" family. Lowercase letters in Table 2 were used to distinguish nucleotides in the constant sequence region and are only shown where they appear to be involved in the secondary structure (duplex) formation (underlined). Ligands that were subjected to the minimal sequence determination analysis (infra) are marked with an asterisk (*) next to the clone number. The clone numbers of ligands that were found to retain high affinity binding as minimal ligands are italicized. All ligands shown in Table 2 were screened for their ability to bind to PDGF AB using the nitrocellulose filter binding method (data not shown).

Minimal sequence determination

Seven of the highest affinity ligands were further characterized by determination of the minimal sequence necessary for high affinity binding. To determine the 3' sequence boundary, a primer that anneals to the 3' fixed sequence of a ligand DNA template was labeled at the 5' end with [γ-$^{32}$P-ATP], annealed to the template, and extended with Sequenase (U.S. Biochemical, Cleveland, Ohio) and a mixture of all four dNTP's and all four ddNTP's to give a population of serially truncated 5' end labeled ligand molecules. This population was reselected for fragments that bind to PDGF AB with high affinity using nitrocellulose filter binding as the partitioning method. The shortest molecules, truncated from the 3' end, that retain high affinity binding were resolved by polyacrylamide gel electrophoresis as described (Jellinek et al., (1994): supra). The 5' sequence boundary was determined by labeling the 3' terminus of the DNA ligands with [α-$^{32}$P]-cordycepin-5'-triphosphate and using lambda exonuclease in a limited digestion to generate a population of serially truncated 3' end labeled ligand molecules. This population, when selected with PDGF AB and resolved by polyacrylamide gel electrophoresis, reveals the shortest molecules truncated from the 5' end to retain high affinity binding (data not shown).

The seven DNA ligands truncated from both ends (indicated by * in Table 2) to the minimal sequence suggested by the above described experiment were synthesized by the solid phase phosphoramidite method (Beaucage and Caruthers (1981) Tetrahedron Lett. 22: 1859), and the equilibrium dissociation constants were determined by nitrocellulose filter binding. The minimal sequences tested were 14t(5'-TACTAGGCTTGACAA AGGGCACCATGGCT-TAGTGGTCCTAGTA<u>T</u>-3'SEQ ID NO: 82 (letter t indicates a truncated ligand and <u>T</u> represents an inverted orientation T (3'-3' linked) (dT-5'-1 caa-CPG 500, Glen Research, Sterling, Va.) introduced to minimize ligand degradation by the 3' to 5' exonucleolytic pathway), 20t-a (5'-T G G G A G G G C G C G T T C T T C G T G G T T A C TTTTAGTCCCGT-3') SEQ ID NO: 83, 20t-b (5'-GGGCGCGTTCTTCGTGGTTACTTTTAGTCCCG<u>T</u>-3') SEQ ID NO: 84, 41t (5'-TACTCAGGGCACT GCAAG-CAATTGTGGTCCCAATGGGCTGAGTA<u>T</u>-3') SEQ ID NO: 85, 36t (5'-CCACAGGCTACGGCA CGTAGAGCAT-CACCATGATCCTGTG<u>T</u>-3') SEQ ID NO: 86, 40t (5'-A G T G G A A C A G G G C A C G G A G A G T - CAAACTTTGGTTTCCCCCACT<u>T</u>-3') SEQ ID NO: 87, 38t (5'-AAGTCGTGCA GGGTCCCCTGGAAGCATCTC-CGATCCCAGACTT<u>T</u>-3') SEQ ID NO: 88, and 26t (5'-TAGAGGGGAAGTAGGCTGCCTGACTCGAGAGAGT <u>T</u>-3') SEQ ID NO: 89. Ligands 14t, 20t-b, 40t, 38t, and 26t bound with substantially lower affinity compared to their full-length analogs (data not shown). Ligands 20t-a, 36t, and 41t, on the other hand, retained high affinity binding to PDGF AB (italicized clone numbers in Table 2).

Binding affinities of three minimal ligands, 20t-a, 36t, and 41t, to PDGF AA, PDGF AB and PDGF BB are summarized in Table 3. All three ligands exhibited very high affinity for PDGF AB and PDGF BB (51–90 pM) and much lower affinity for PDGF AA (48–72 nM). It is concluded from the binding data that these three ligands bind preferentially to the PDGF B chain, with an affinity differential of about $10^3$. As an example, plot of the binding data for the minimal ligands 20t-a, 36t, 41t and TH38 (ligand that was evolved to bind with high affinity to human thrombin: 5'-CAGTCCGTGGTAGGGCAGGTTGGGGTGACTTCG TGGAA<u>T</u>-3') SEQ ID NO: 90 to PDGF AB is shown in FIG. 1.

The binding data were analyzed according the formalism described in Jellinek et al., 1994: supra. Binding of ligands 20t-a, 36t, and 41t to PDGF AB (FIG. 1) and PDGF BB (not shown) is biphasic and the values of the dissociation constant that correspond to the higher affinity interaction are shown in Table 3. Biphasic binding has been observed previously and interpreted it as a consequence of the existence of two species of oligonucleotide that bind to the target protein with different affinities (Jellinek et al., 1993, 1994: supra). In all cases, the mole fraction of the high affinity binding component was >0.6.

EXAMPLE 3

EXPERIMENTAL PROCEDURE FOR EVOLVING 2'-FLUORO-2'-DEOXYPYRIMIDINE RNA LIGANDS TO PDGF AND RNA SEQUENCES OBTAINED

2'-FLUORO-2'-DEOXYPYRIMIDINE RNA SELEX

SELEX with 2'-fluoro-2'-deoxypyrimidine RNA targeting PDGF AB was done essentially as described previously (vide supra, and Jellinek et al,, 1993, 1994: supra) using the primer template set as shown in Table 4 SEQ ID NO: 36. Briefly, the 2'-fluoro-2'-deoxypyrimidine RNA for affinity selections was prepared by in vitro transcription from synthetic DNA templates using T7 RNA polymerase (Milligan et al. Nucl. Acids Res,, 15: 8783 (1987)). The conditions for in vitro transcription described in detail previously (Jellinek et al. (1994) supra) were used, except that higher concentration (3 mM) of the 2'-fluoro-2'-deoxypyrimidine nucleoside triphosphates (2'-F-UTP and 2'-F-CTP) was used compared to ATP and GTP (1 mM). Affinity selections were done by incubating PDGF AB with 2'-fluoro-2'-deoxypyrimidine RNA for at least 15 min at 37° C. in PBS containing 0.01% human serum albumin. Partitioning of free RNA from protein-bound RNA was done by nitrocellulose filtration as described (Jellinek et al., 1993, 1994: supra). Reverse transcription of the affinity-selected RNA and amplification by PCR were done as described previously SEQ ID NOS: 37-38 (Jellinek et al. (1994) supra). Nineteen rounds of SELEX were performed, typically selecting between 1–12% of the input RNA. For the first eight rounds of selection, suramin (3–15 µM) was included in the selection buffer to increase the selection pressure. The affinity-enriched pool (round 19) was cloned and sequenced as described (Schneider et al., 1992 supra). Forty-six unique sequences have been identified, and the sequences are shown in Table 5. SEQ ID NOS: 39–81 the unique-sequence ligands were screened for their ability to bind PDGF AB with high affinity. While random 2'-fluoropyrimidine RNA (Table 4) bound to PDGF with a dissociation constant (Kd) of 35±7 nM, many of the affinity-selected ligands bound to PGDF AB with ≈100-fold higher affinities. Among the unique ligands, clones 9 ($K_d$=91±16 pM), 11 ($K_d$=120±21 pM), 16 ($K_d$=116±34 pM), 23 ($K_d$=173±38 pM), 25 ($K_d$=80±22 pM), 37 ($K_d$=97±29 pM), 38 ($K_d$=74±39 pM), and 40 ($K_d$=91±32 pM) exhibited the highest affinity for PDGF AB (binding of all of these ligands to PDGF AB is biphasic and the $K_d$ for the higher affinity binding component is given).

TABLE 1

Starting DNA and PCR primers for the ssDNA SELEX experiment.

| | SEQ ID NO. |
|---|---|
| Starting ssDNA:<br>5'-ATCCGCCTGATTAGCGATACT[-40N-]ACTTGAGCAAAATCACCTGCAGGGG-3' | 1 |
| PCR Primer 3N2*:<br>5'-BBBCCCCTGCAGGTGATTTTGCTCAAGT-3' | 2 |
| PCR Primer 5N2**:<br>5'-CCGAAGCTTAATACGACTCACTATACTAGGGATCCGCCTGATTAGCGATACT-3' | 3 |

*B = biotin phosphoramidite (e.g., Glen Research, Sterling, VA)
**For rounds 10, 11, and 12, the truncated PCR primer 5N2 (underlined) was used to amplify the template.

TABLE 2

Sequences of the ssDNA high affinity ligands to PDGF.

| | | SEQ ID NO |
|---|---|---|
| FAMILY 1 | | |
| *14 | tactAGGCTTGACAAAGGGCACC-ATGGCTT-AGT---GGTCCTAGTa | 4 |
| *41 | tactCAGGGCACTGCAAGC---AATTGTGGTCCCAAT-GGGCTGAGTa | 5 |
| 6 | tactCCAGGCAGTCATGGTC---ATTGTTTACAGTC----GTGGAGTAGGT | 6 |
| FAMILY 2A | | |
| 23 | AGGTGATCCCTGCAAAGGC--------AGGATAACGTCCTG----AGCATCac | 7 |
| 2 | ATGTGATCCCTGCAGAGGG--------AGGAN-ACGTC-TG----AGCATCac | 8 |
| 34 | CACGTGATCCCAT--AAGGGCTGCCG------AAAATAGCAG-----AGCATCac | 9 |
| 8 | GGTGGAC----TAGAGGGCAGC------AAACGATCCTTGGTT-AGCGTCCac | 10 |
| FAMILY 2B | | |
| 1 | GGTGCGAC-----GAGGC-----TTACACAAACGTACACGTTTCCCCGCac | 11 |
| 5 | TGTCGGAGC-----AGGGGCG-TACGA----AAACTTTACAGTTCCCCCGac | 12 |
| *40 | AGTGGAA------CAGGGCACGGAGAGTC-AAACTTTG-GTTTCCCCCact | 13 |
| FAMILY 2C | | |
| 47 | GTGGG-------TAGGGATCGGTGGATGCCTCG-TCACTTCTAGTCCCac | 14 |
| 18 | ctGGG--------CGCCCTAAACAAAGGGTGG-TCACTTCTAGTCCCAGGA | 15 |
| 30 | TCCGGG------CTCGGGA-------TTCGTGG-TCACTTTCAGTCCCGGATATA | 16 |
| *20 | ATGGGA--------GGGCGCG--TTCTTCGTGG-TTACTTTTAGTCCCG | 17 |
| 35 | ACGGGA---------GGGCACG--TTCTTCGTGG-TTACTTTTAGTCCCG | 18 |
| 13 | GCTCGTAGG--------GGGCGA---TTCTTTCGCCGTTACTTCCAGTCCTac | 19 |
| FAMILY 3 | | |
| 16 | ctGAGGCAT-GTTAACAT--GAGCATCGTCTCAC--GATCCTCAGCC | 20 |
| *36 | CCACAGGCT-ACGGCACGTA-GAGCATCACC-AT---GATCCTGTG | 21 |
| 50 | GCGGGCAT--GGCACAT--GAGCATCTCT------GATCCCGCAATCCTC | 22 |
| 4 | ACCGGGCT---ACTTCGT-AGAGCATCTCT------GATCCCGGTGCTCG | 23 |

TABLE 2-continued

Sequences of the ssDNA high affinity ligands to PDGF.

| | | SEQ ID NO |
|---|---|---|
| 44 | AAAGGGCGAACGTAGGTC-GAGGCATC---CATTG-GATCCCTTC | 24 |
| 24 | ACGGGCTCT--GTCACT-GTGGCACTAGCAATA--G-TCCCGTCGC | 25 |
| 7 | tGGGCAGACCTTCTGGACGAGCATCACCTATGT-GATCCCG | 26 |
| OTHER SEQUENCES | | |
| *26 | AGAGGGGAAGTAGGCTGCCTGACTCGAGAGAGTCCCG | 27 |
| 19 | AGGGGTGCGAAACACATAATCCTCGCGGA---TTCCCATCGCT | 28 |
| 48 | GGGGGGGCAATGGCGGTACCTCT-------GGTCCCCTAAATAC | 29 |
| 46 | ctGCGG-CTCAAA-GTCCT--GCTACCCGCAGCACATCTGTGGTC | 30 |
| 25 | cfTTGGGCGTGAATGTCCACGGGTACCTCCGGTCCCAAAGAG | 31 |
| 31 | TCCGCGCAAGT-CCC---TGGTAAAGGGCAGCCCTAACTGGTC---acttgagc | 32 |
| 12 | ctCAAGTTCCCCACAAGACTGGGGCTGTTCAAACCGCTAGTAacttgag | 33 |
| 15 | ctCAAGTAGGGCGCGACACACGTCCGGGCACCTAAGGTCCCAacttgag | 34 |
| *38 | AAAGTCGTGCAGGGTCCCCTGGAAGC-ATCTCCGATCCCAGactt | 35 |

TABLE 3

Affinities of the truncated ssDNA ligands to PDGF AA, PDGF AB and PDGF BB.

| | $K_d$, nM | | |
|---|---|---|---|
| Ligand | PDGF AA* | PDGF AB** | PDGF BB** |
| 20t-a | 48 ± 4 | 0.082 ± 0.008 | 0.090 ± 0.007 |
| 36t | 72 ± 12 | 0.082 ± 0.013 | 0.054 ± 0.013 |
| 41t | 50 ± 8 | 0.051 ± 0.015 | 0.056 ± 0.010 |

*Data points were fit to a monophasic binding equation (Jellinek et al., (1994): supra).
**Data points were fit to a biphasic binding equation (Jellinek et al., (1994): supra). The dissociation constant ($K_d$) shown relates to the higher affinity component. The mole fraction of DNA that binds to PDGF AB or PDGF BB as the high affinity component ranges between 0.61 to 0.79. The $K_d$ values for the lower affinity interaction range between 2 to 28 nM.

TABLE 4

Starting RNA and PCR primers for the 2'-fluoropyrimidine RNA SELEX experiment.

| | SEQ ID NO |
|---|---|
| Starting 2'-fluoropyrimidine RNA: | |
| Starting RNA: | |
| 5'-GGGAGACAAGAAUAACGCUCAA[-50 N-]UUCGACAGGAGGCUCACAACAGGC-3' | 36 |
| PCR Primer 1: | |
| 5'-TAATACGACTCACTATAGGGAGACAAGAATAACGCTCAA-3' | 37 |
| PCR Primer 2: | |
| 5'-GCCTGTTGTGAGCCTCCTGTCGAA-3' | 38 |

TABLE 5

Sequences of the 2'-fluoropyrimidine RNA high affinity ligands to PDGF AB.

| | | SEQ ID NO. |
|---|---|---|
| 1 | CGGUGGCAUUUCUUCACUUCCUUCUCGCUUUCUCGCGUUGGGCLNCGA | 39 |
| 2 | CCAACCUUCUGUCGGCGUUGCUUUUUGGACGGCACUCAGGCUCCA | 40 |
| 3 | UCGAUCGGUUGUGUGCCOGACAGCCUUAACCAGGGCUGGGACCGAGGCC | 41 |
| 4 | CUGAGUAGGGGAGGAAGUUGAAUCAGUUGUGGCGCCUCUCAUUCGC | 42 |
| 5 | CAGCACUUUCGCUUUUCAUCAUUUUUUCUUUCCACUGUUGGGCGCGGAA | 43 |

TABLE 5-continued

Sequences of the 2'-fluoropyrimidine RNA high affinity ligands to PDGF AB.

| | | SEQ ID NO. |
|---|---|---|
| 6 | UCAGUGCUGGCGUCAUGUCUCGAUGGGGAUUUUUCUUCAGCACUUUGCCA | 44 |
| 7 | UCUACUUUCCAUUUCUCUUUUCUUCUCACGAGCGGGUUUCCAGUGAACCA | 45 |
| 8 | CGAUAGUGACUACGAUGACGAAGGCCGCGGGUUGGAUGCCCGCAUUGA | 46 |
| 10 | GUCGAUACUGGCGACUUGCUCCAUUGGCCGAUUAACGAUUCGGUCAG | 47 |
| 13 | GUGCAAACUUAACCCGGGAACCGCGCGUUUCGAUCGACUUUCCUUUCCA | 48 |
| 15 | AUUCCGCGUUCCGAUUAAUCCUGUGCUCGGAAAUCGGUAGCCAUAGUGCA | 49 |
| 16 | CGAACGAGGAGGGAGUGGCAAGGGAUGGUUGGAUAGGCUCUACGCUCA | 50 |
| 17 | GCGAAACUGGCGACUUGCUCCAUUGGCCCAUAUAACGAUUCGGUUCAU | 51 |
| 18 | CGAACGAGGAGGGAGUCGCAAGGGAUGGUUGGAUAGGCUCUACGCUCAA | 52 |
| 19 | CGAGAAGUGACUACGAUGACGAAGGCCGCGGGUUGAAUCCCUCAUUGA | 53 |
| 20 | AAGCAACGAGACCUGACGCCUGAUGUGACUGUGCUUGCACCCGAUUCUG | 54 |
| 21 | GUGAUUCUCAUUCUCAAUGCUUUCUCACAACUUUUUUCCACUUCAGCGUGA | 55 |
| 22 | AAGCAACGAGACUCGACGCCUGAUGUGACUGUGCUUGCACCCCAUUCU | 56 |
| 23 | UCGAUCGGUUGUGUGCCGGACAGCUUUGACCAUGAGCUGGGACCGAGGCC | 57 |
| 24 | NGACGNGUGGACCUGACUAAUCGACUGAUCAAAGAUCCCGCCCAGAUGGG | 58 |
| 26 | CACUGCGACUUGCAGAAGCCUUGUGUGGCGGUACCCCCUUUGGCCUCG | 59 |
| 27 | GGUGGCAUUUCUUCAUUUUCCUUCUCGCUUUCUCCGCCGUUGGGCGCG | 60 |
| 29 | CCUGAGUAGGGGGGAAAGUUGAAUCAGUUGUGGCGCUCUACUCAUUCGCC | 61 |
| 30 | GUCGAAACUGGCGACUUGCUCCAUUGGCCGAUAUAACGAUUCGGUUCA | 62 |
| 31 | GCGAUACUGGCGACUUGCUCCAUUGGCCGAUAUAACGAUUCGGCUCAG | 63 |
| 32 | ACGUGGGGCACAGGACCGAGAGUCCCUCCGGCAAUAGCCGCUACCCCACC | 64 |
| 33 | CACAGCCUNANAGGGGGGAAGUUGAAUCAGUUGUGGCGCUCUACUCAUUCGC | 65 |
| 34 | ANGGGNUAUGGUGACUUGCUCCAUUGGCCGAUAUAACGAUUCGGUCAG | 66 |
| 35 | CCUGCGUAGGGNGGGAAGUUGAAUCAGUUGUGGCGCUCUACUCAUUCGCC | 67 |
| 39 | CGAACGAGGAGGGAGUGGCAAGGGAUGGUUGGAUAGGCUCUACGCUCA | 68 |
| 41 | GUGCAAACUUAACCCGGGAACCGCGCGUUUCGAUUCGCUUUCCNUAUUCCA | 69 |
| 42 | CGAACGAGGAGGGAGUGGCAAGGGACACGCGUGAGCUUCGCACACAUCUGC | 70 |
| 43 | UCGGUGUGGCUCAGAAACUGACACGCGUGAGCUUCGCACACAUCUGC | 71 |
| 44 | UAUCGCUUUUCAUCAAUUCCACUUUUUCACUCUNUAACUUGGGCGUGCA | 72 |
| 45 | GUGCAAACUUAACCCGGGAACCGCGCGUUUCGAUCCUGCAUCCUUUUUCC | 73 |
| 46 | UCGNUCGGUUGUGUGCCGGCAGCUUUGUCCAGCGUUGGGCCGAGGCC | 74 |
| 47 | AGUACCCAUCUCAUCUUUUCCUUUCCUUUCUUCAAGGCACAUUGAGGGU | 75 |
| 49 | CCUGAGUAGGGGGGGAAGUUGAACCAGUUGUGGCNGCCUACUCAUUCNCCA | 76 |
| 51 | CCNNCCUNCUGUCGGCGCUUGUCUUUUUGGACGGGCAACCCAGGGCUC | 77 |
| 52 | CCAACCUNCUGUCGGCGCUUGUCUUUUUGGACGAGCAACUCAAGGCUCGU | 78 |
| 53 | CCAGCGCAGAUCCCGGGCUGAAGUGACUGCCGGCAACGGCCGCUCCA | 79 |
| 54 | UUCCCGUAACAACUUUUCAUUUUCACUUUUCAUCCAACCAGUGAGCAGCA | 80 |
| 55 | UAUCGCUUUCAUCAAAUUCCACUCCUUCACUUCUUUAACUUGGGCGUGCA | 81 |

---

We claim:

1. A purified and isolated non-naturally occurring nucleic acid ligand to PDGF.

2. The purified and isolated non-naturally occurring nucleic acid ligand of claim 1 wherein said nucleic acid ligand is single-stranded.

3. The purified and isolated non-naturally occurring nucleic acid ligand of claim 2 wherein said nucleic acid ligand is RNA.

4. The purified and isolated non-naturally occurring nucleic acid ligand of claim 2 wherein said nucleic acid ligand is DNA.

5. A nucleic acid ligand to Platelet Derived Growth Factor (PDGF) identified according to the method comprising:

a) contacting a candidate mixture of nucleic acids with PDGF, wherein nucleic acids having an increased affinity to PDGF relative to the candidate mixture may be partitioned from the remainder of the candidate mixture;

b) partitioning the increased affinity nucleic acids from the remainder of the candidate mixture; and c) amplifying the increased affinity nucleic acids to yield a mixture of nucleic acids enriched for nucleic acid sequences with relatively higher affinity and specificity for binding to PDGF, whereby a nucleic acid ligand of PDGF may be identified.

6. The purified and isolated non-naturally occurring RNA ligand to PDGF of claim 3 wherein said ligand is selected from the group consisting of the sequences set forth in Table 5 (SEQ ID NOS: 39–81).

7. The purified and isolated non-naturally occurring DNA ligand to PDGF of claim 4 wherein said ligand is selected from the group consisting of the sequences set forth in Table 2 (SEQ ID NOS: 4–35).

* * * * *